United States Patent [19]

Holla et al.

[11] Patent Number: 5,380,659
[45] Date of Patent: Jan. 10, 1995

[54] PROCESS FOR HIGHLY REGIOSELECTIVE ESTERIFICATION AND ESTER CLEAVAGE ON UNSATURATED SUGAR COMPOUNDS WITH THE AID OF LIPASES AND ESTERASES

[75] Inventors: Wolfgang Holla, Hofheim am Taunus; Reinhold Keller, Bad Soden am Taunus, both of Germany

[73] Assignee: Hoechst Aktiengesellschaft, Frankfurt am Main, Germany

[21] Appl. No.: 924,799

[22] Filed: Aug. 6, 1992

Related U.S. Application Data

[63] Continuation of Ser. No. 336,480, Apr. 12, 1989, abandoned.

[30] Foreign Application Priority Data

Apr. 14, 1988 [DE] Germany .................... 3812409
Aug. 19, 1988 [DE] Germany .................... 3828190

[51] Int. Cl.⁶ .......................... C12N 9/16; C12N 9/18; C12N 9/20; C12P 7/00
[52] U.S. Cl. .................... 435/196; 435/132; 435/197; 435/198; 435/280; 435/921
[58] Field of Search ............... 435/196, 132, 280, 198, 435/197, 196, 921

[56] References Cited

PUBLICATIONS

Cambone et al., *Biotech & Bioeng.*, vol. 26, pp. 1449–1454 (1984).
Hehre et al., *Biochem.*, vol. 16(9), pp. 1780–1786 (1977).
Wentworth et al., *Biochem.*, vol. 13(23), pp. 4715–4720 (1974).
Baratti et al., "Enantioselective Synth. of Fatty Acid Esters by Lipases," Proc.-World Conf. Biotechnol. Fats Oils Ind., Meeting Date 1987, pp. 355–358 (1988).
Anthony F. Hadfield et al., Carbohydrate Research, 101 (1982), pp. 197–208.
E. Wolfgang Holla, Agnew, Chem. Int. Ed. Engl. 28 (1989), No. 2, pp. 220 and 221.
M. Therisod et al., J. Am. Chem. Soc., vol. 108, (1986), S. 5638 ff.
H. M. Sweers et al., J. Am. Chem. Soc., vol. 108, (1986), S. 6421 ff.
M. Kloosterman et al., Tetrahedron Letters, vol. 28, No. 26, (1987), S. 2989 ff.
J. F. Shaw et al., Biotech and Bioeng., vol. 29, (1987), S. 648 ff.

*Primary Examiner*—Ronald W. Griffin
*Attorney, Agent, or Firm*—Finnegan, Henderson, Farabow, Garrett & Dunner

[57] ABSTRACT

A process for highly regioselective esterification and ester cleavage on unsaturated sugar compounds with the aid of lipases and esterases, and products which can be prepared by this process.

Highly regioselective esterifications and ester cleavages can be carried out on unsaturated sugar compounds with the aid of lipases and esterases. Lipases from microorganisms or from the pancreas and liver of animals are preferably used.

17 Claims, No Drawings

PROCESS FOR HIGHLY REGIOSELECTIVE ESTERIFICATION AND ESTER CLEAVAGE ON UNSATURATED SUGAR COMPOUNDS WITH THE AID OF LIPASES AND ESTERASES

This application is a continuation of application Ser. No. 07/336,480 filed Apr. 12, 1989, now abandoned.

DESCRIPTION

A process for highly regioselective esterification and ester cleavage on unsaturated sugar compounds with the aid of lipases and esterases, and products which can be prepared by this process.

Unsaturated sugars are widely used as building blocks in synthesis, for example for the preparation of glyco conjugates, disaccharides, oligosaccharides, 2-deoxy sugars, amino sugars, thromboxanes and the lactone moiety of compactin.

The regioselective transformations and modifications of the unsaturated sugars which are required for these syntheses often represent a problem in organic chemistry and necessitate difficult or elaborate reaction sequences. The regioselective chemical acylation of the large number of hydroxyl groups necessitates time-consuming introduction and subsequent elimination of specific protective groups.

It is known that regioselective esterifications and ester cleavages can be carried out on the primary hydroxyl groups of simple saturated sugars with the aid of selected lipases [Therisod M., Klibanov A. M., J. Am. Chem. Soc. 108, 5638, (1986); Sweers H. M., Wong C. H., J. Am. Chem. Soc. 108, 6421 (1986); Kloosterman M. et al. Tetrahedron Letters 28, 2989 (1987)]. The reactions described by Therisod and Klibanov require large excesses of enzyme and reaction times of at least two days, and the conversions are usually below 50%.

Sweers and Wong describe the regioselective enzymatic cleavage of 2,3,4,6-tetra-0-acyl-D-hexopyranosides to the 6-OH derivative. However, the acyl radicals are long-chain esters. Kloostermann has described the regioselective deacetylation of methyl 2,3,4,6-tetra-0-acetyl-α-D-glucopyranoside.

The enzymatic ester cleavages of monosaccharide pentaacetates result in complex mixtures of various regioisomers. Thus, Shaw and Klibanov [Biotech. Bioeng. 29, 648 (1987)] obtain gram quantities of glucose 2,3,4,6-tetraacetate, glucose triacetate, specifically a mixture of 2,4,6- and 3,4,6-triacetate, and glucose 4,6-diacetate.

It has now been found that unsaturated sugars can, with the aid of lipases and esterases, be regiospecifically or regioselectively esterified or, depending on the conditions, the ester linkages can also be cleaved. This is particularly surprising because enzymes are known to react only with particular substrates.

Unsaturated sugars represent a new substrate for lipases. They are more sensitive than saturated sugars, and have a different spatial structure and an additional functional group. This is why it was not predictable that these reactions would take place at all and certainly not that they can be carried out in such an economic manner.

Hence the invention relates to a process for esterification and ester cleavage with the aid of lipases and esterases, which comprises use of unsaturated sugar compounds of the general formula I

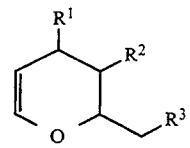

in which
a) $R^1$, $R^2$ and $R^3$ are ($C_1$ to $C_{10}$)-acyloxy whose carbon atoms can be substituted with halogen and/or amino and/or methoxy and/or phenyl and/or phenoxy, and/or are benzoyloxy whose carbon atoms can be substituted with nitro and/or halogen and/or ($C_1$ and $C_2$)-alkoxy
b) $R^1$, $R^2$ and $R^3$ are hydroxyl,
c) $R^1$ is a protected hydroxyl and $R^2$ and $R^3$ are ($C_1$–$C_{10}$)-acyloxy and/or benzoyloxy,
d) $R^1$ and $R^3$ are ($C_1$–$C_{10}$)-acyloxy and/or benzoyloxy and $R^2$ is a protected hydroxyl,
e) $R^1$ is a protected hydroxyl and $R^2$ and $R^3$ are hydroxyl,
f) $R^1$ and $R^3$ are hydroxyl and $R^2$ is protected hydroxyl,
g) $R^1$ and $R^2$ are hydroxyl and $R^3$ is ($C_1$–$C_{10}$)-acyloxy, benzoyloxy or a protected hydroxyl and
h) $R^1$ and $R^2$ are acyloxy and/or benzoyloxy and $R^3$ is a protected hydroxyl, it being possible for acyloxy and benzoyloxy each to be substituted as defined under a). The invention also relates to the compounds of the general formula I in which
i) $R^1$ is hydroxyl and $R^2$ and $R^3$ are ($C_1$–$C_{10}$)-acyloxy and/or benzoyloxy,
j) $R^1$ and $R^3$ are ($C_1$–$C_{10}$)-acyloxy and/or benzoyloxy and $R^2$ is hydroxyl,
k) $R^1$ and $R^2$ are hydroxyl and $R^3$ is ($C_1$–$C_{10}$)-acyloxy or benzoyloxy, and the derivatives thereof with a protected hydroxyl group, it being possible for acyloxy and benzoyloxy each to be substituted as defined under a). The invention also relates to the use of these compounds as intermediates.

The invention is described in detail hereinafter, especially in its preferred embodiments. The invention is also defined in the claims.

The unsaturated compound of the general formula I can be bought (glucal and galactal and the triacetyl compounds thereof: 3,4,6-tri-0-acetyl-1,5-anhydro-2-deoxy-arabino-hex-1-enitol or 3,4,6-tri-0-acetyl-1,5-anhydro-2-deoxylyxo-hex-1-enitol) or can easily be obtained by chemical synthesis [Roth W., Pigman W., Methods Carbohydr. Chem. 2, 405 (1963)].

The protected derivatives of the unsaturated sugar compounds of the general formula I are essentially a) acetals, preferably, for example, tetrahydropyranyl ethers (THP ethers), methoxymethyl ethers (MOM ethers), methythiomethyl ethers (MTM ethers), 2-methoxyethoxymethyl ethers (MEM ethers), 2-(trimethylsilyl)ethoxymethyl ethers (SEM ethers) and 1-ethoxyethyl ethers, or b) ethers, preferably, for example, methyl ethers, benzyl ethers, trimethylsilyl ethers, tertiarybutyldimethylsilyl ethers, tertiary-butyldiphenylsilyl ethers and allyl ethers, and c) esters, preferably, for example acetates, chloroacetates, trifluoroacetate, benzoates, pivalate, trifluoromethanesulfonates, methanesulfonates and toluenesulfonates.

Acyloxy is to be understood to include groups having 1 to 10 carbon atoms, preferably 1 to 5 carbon atoms.

These carbon atoms can be substituted with halogen, amino, methoxy, phenyl and/or phenoxy. Benzoyloxy can be substituted with nitro, halogen and/or ($C_1$ and $C_2$)-alkoxy.

It is possible according to the invention to use in the process lipases and esterases preferably obtained from microorganisms or the pancreas or liver of animals. Particular preferred are lipases and esterases from Pseudomonas, Candida, Mucor, Rhizopus, Penicillium and Aspergillus, and from pig liver and pig pancreas. The enzymes can be bought or can be extracted by known methods from the appropriate microorganism or from the liver or the pancreas. The reaction can also be carried out with whole cells of the said microorganisms as long as they contain the enzyme necessary for this. It is then, in certain circumstances, advantageous to make the cells permeable with the aid of methods known per se so that the enzymes can gain access to the substrate more easily.

The best procedure for the enzymatic esterification is as follows:

The compounds Ib, e, f or g are dissolved in a solvent, for example ethyl acetate, dimethoxyethane, tetrahydrofuran, tert. butyl methyl ether or methyl ethyl ketone, and then the benzoyl or acyl donor is added, for example a carboxylic ester, preferably a vinyl ester such as, for example, vinyl acetate, vinyl benzoate, vinyl chloroacetate, vinyl methoxyacetate, vinyl phenoxyacetate, vinyl phenylacetate, amino acid vinyl esters for example Z-glycine vinyl ester, or isopropenyl acetate or instead of carboxylic esters carboxylic anhydrides, e.g. pivalic anhydride, acetic anhydride and benzoic anhydride. It is, however, also possible to use the benzoyl or acyl donor simultaneously as the solvent. The lipase or esterase is added in free or immobilized form, and incubation is carried out at temperatures between 0° and 80° C., preferably between 10° and 50° C.

Suitable for immobilizing the enzymes are all the conventional processes described in the literature [W. Hartmeier, Trends in Biotechnology 3, 149 (1985); A. Rosevaer, J. Chem. Tech. Biotechnol. 34B, 127 (1984)]. Immobilized and free enzymes can also be used in a column process.

The reaction times depend on the structure and solubility of the unsaturated sugar, on the temperature and on the concentration ratios, especially on the quantity of enzyme. They can be between 0.5 hours and 3 days, but are usually between 5 and 24 hours.

The reactions are usually worked up by separating off, for example filtering off, the free or immobilized enzyme, distilling off the solvents and/or the acyl donors in vacuo, and purifying the products, where necessary, by crystallization, chromatography or extraction.

For the enzymatic hydrolysis the compounds Ia, c, d, f or h are added in pure or dissolved form to a buffered aqueous solution, and the desired enzyme is added. It is possible to operate both at a constant pH and without pH control in the range from about 4 to 8. After the reaction is complete, the desired product is obtained by extraction or after freeze-drying and separating off enzyme and concomitant salts by, for example, filtration or chromatography.

Particular reactions are advantageously carried out with particular enzymes, especially to achieve the best reaction rates and yields. The ester cleavage of the compound with the formula Ia in which $R^1$, $R^2$ and $R^3$ denotes acyloxy and/or benzoyloxy is preferably carried out with lipases or esterases from Pseudomonads. The reaction product is the compound of the formula Ii in which $R^1$ denotes hydroxyl and $R^2$ and $R^3$ denote acyloxy and/or benzoyloxy. In turn, the esterification can be advantageously carried out with the aid of Pseudomonas or Candida lipases or esterases, but the main final products are different. Incubation of the compound of the formula Ib in which $R^1$, $R^2$ and $R^3$ denote hydroxyl with the enzyme from Pseudomonas results in the compound of the formula Ij in which $R^1$ and $R^3$ denote acyloxy and/or benzoyloxy and $R^2$ denotes hydroxyl. The transfer of benzoyl groups to $R^1$ is, however, slower than the transfer of acyl groups, most probably for steric reasons, so that Pseudomonas lipases can also be used to form the 6-0-monobenzoate. The compound of the formula Ik in which $R^1$ and $R^2$ denote hydroxyl, and $R^3$ is acyloxy or benzoyloxy, can be obtained with Candida lipases.

The resulting compounds Ii, j, and k can be chemically derivatized by methods known per se with the aid of the abovementioned protective groups (T. W. Greene, Protective Groups in Organic Synthesis, John Wiley & Sons, 1981) so that they can then be used either in organic chemical reactions and/or in renewed regioselective esterifications or ester cleavages with lipases and esterases. Thus, for example, the compound of the formula I in which $R^1$ represents a protected hydroxyl group and $R^2$ and $R^3$ represent an acyloxy group is prepared chemically, and the acyl group is eliminated from $R^3$ with the aid of the lipases and esterases so that $R^3$ then denotes hydroxyl. Preferably used in these reactions are Candida, Pseudomonas, Mucor and pancreatic lipases or esterases.

In the case of compound Ij it is likewise possible to introduce a protective group in $R^2$. If compounds of this type are then preferably treated with the enzyme from Pseudomonas or Candida, 2 different products result. With the aid of the former the compound of the formula I in which $R^1$ is hydroxyl, $R^2$ is a protected hydroxyl group and $R^3$ is acyloxy is obtained, and with the aid of the Candida lipase the compound of the formula I in which $R^1$ denotes acyloxy, $R^2$ denotes a protective hydroxyl group and $R^3$ denotes a hydroxyl group is obtained.

The surprising deduction to be made from the abovementioned observations is that Pseudomonas lipases or esterases preferentially attack the secondary functional group $R^1$ in compounds of the formula I, whereas Candida lipases or esterases preferentially attack the primary functional group $R^3$. In the case of enzymatic esterifications it is also possible to use in place of Pseudomonas lipases or esterases, where appropriate, lipases or esterases from Mucor, Rhizopus and Penicillium species to catalyze the attack on $R^1$ in compounds of the formula Ib, f, g and i, and for hydrolyses on $R^1$ in compounds of the formula Ia, d, h and j in individual cases also lipases from pig pancreas apart from those mentioned.

The advantages of the process according to the invention lie in the unexpected regioorientation of the higher regioselectivity and, associated therewith, the uniformity of the product, the high reaction rate as well as the high yield and the easy working up.

The invention is described in more detail by means of the examples which follow. Unless otherwise indicated, percentage data relate to weight.

EXAMPLES

1. Preparation of 6-0-acetylglucal 1.022 g (7 mmol) of glucal are taken up in 2 ml of ethyl acetate and 30 ml of vinyl acetate, 400 mg of lipase from Candida cylindracea lipase OF (Meito Sangyo Co. Ltd.) are added, and the mixture is stirred at room temperature overnight. After the reusable enzyme has been separated off, and subsequent chromatography or crystallization, 1.12–1.25 g of 6-0-acetylglucal (85–95% yield) are obtained.

2. Preparation of 6-0-acetyl-3-0-tert.-butyldimethylsilyl-glucal 1.09 g (5 mmol) of 3-0-tert.-butyldimethylsilyl-glucal are taken up in about 10 ml of ethyl acetate and 50–70 ml of vinyl acetate, and 1 g of lipase from Candida cylindracea (Sigma) is added. After stirring at room temperature for about 20–24 h, the reusable enzyme is filtered off.

Concentration in vacuo and subsequent simple filtration through a silica gel column (in hexane or ether/hexane v:v) yields 1.0–1.2 g of the desired 6-0-acetyl-3-0-tert.-butyldimethylsilyl-glucal (80–90% yield).

3. Preparation of 6-0-acetyl-4-0-tert.-butyldimethylsilyl-glucal 1.09 g (5 mmol) of 4-0-tert.-butyldimethylsilyl-glucal are taken up in 10–20 ml of ethyl acetate and 50–80 ml of vinyl acetate, and 1.0 g of lipase from Candida cylindracea (Sigma) is added. After stirring at room temperature for 20–24 hours, the reusable enzyme is filtered off, and the solution is concentrated in vacuo. Subsequent simple filtration through a silica gel column in ether/hexane (~1:1 v:v) yields 1.1–1.2 g of 6-0-acetyl-4-0-tert.-butyldimethylsilyl-glucal (85–90% yield).

4. Preparation of 6-0-acetylgalactal 1.0 g (6.85 mmol) of galactal is dissolved in about 1 ml of water, and 1–4 g of crushed molecular sieves, 25–75 ml of vinyl acetate and 800 mg of lipase from Candida cylindracea (Sigma) are added. The mixture is stirred at room temperature for about 45 min. Drying, filtration, concentration in vacuo and chromatography on silica gel (ethyl acetate/hexane 1:1) or crystallization (from ethyl acetate/hexane) yields 1.090 to 1.160 (85–90%) of the desired 6-0-acetylgalactal.

5. Preparation of 4,6-di-0-acetylglucal 7.0 g (30 mmol) of tri-0-acetylglucal in 70 ml of 0.25 M phosphate buffer (pH=7) are stirred with 7 g of lipase from Pseudomon as spec. (Lipase P, from Amano Pharmaceutical Co., Ltd., Nagoya, Japan) (free or immobilized on $SiO_2$) at room temperature. After the reaction is complete (about 5–7 h) the reusable enzyme is separated off. The desired 4,6-di-0-acetylglucal is obtained either by extraction of the aqueous solution with $CHCl_3$ or ethyl acetate or after freeze-drying and subsequent taking up in organic solvents such as ethyl acetate and filtering off the insoluble concomitants. The 4,6-di-0-acetylglucal which results in about 90% yield can be used without further purification for further reactions.

6. Preparation of 3,6-di-0-acetylglucal 7.3 g (50 mmol) of glucal are taken up in 50 ml of ethyl acetate and 150 ml of vinyl acetate and stirred at room temperature with 2 g of lipase from Pseudomonas spec. (lipase P, from Amano Pharmaceutical Co., Ltd., Nagoya, Japan). After the reaction is complete (TLC check, about 48 h) the reusable enzyme is filtered off, and the solvent is evaporated. The 3,6-di-0-acetylglucal which results in more than 90% yield can be used without further purification for synthetic purposes.

7. Preparation of 3,6-di-0-acetylgalactal 1.0 g (6.85 mmol) of galactal is dissolved in about 1 ml of water, 1–4 g of crushed molecular sieves, 25–75 ml of vinyl acetate and 1.0 g of lipase from Pseudomonas spec. (Amano) are added and the mixture is stirred at room temperature overnight. Drying, filtration and chromatography on silica gel (ethyl acetate/hexane 2:3, v:v) result in 1.1 to 1.26 g (70–80%) of 3,6-di-0-acetylgalactal.

8. Preparation of 3,6-di-0-acetylglucal 1.02 g (7 mmol) of glucal, 0.5–0.7 ml of $H_2O$ and about 2 g of crushed molecular sieves are taken up in 25–50 ml of isopropenyl acetate, and 1 g of lipase from Pseudomonas spec. is added and the mixture is stirred at room temperature for 25–30 h. Filtration and concentration in vacuo are followed by chromatography on silica gel (ethyl acetate/hexane 2:3, v:v). 0.97–1.05 g (60–65%) of 3,6-di-0-acetylglucal are obtained.

9. Preparation of 3-0-acetyl-6-0-tert.butyldimethylsilyl-glucal 1.0 g (4 mmol) of 6-0-tert.butyldimethylsilyl-glucal in 5–10 ml of vinyl acetate is stirred with 1.0 g of lipase from Pseudomonas spec. at room temperature for 3–4 hours. Filtration, concentration and chromatography ($SiO_2$, ether/hexane 1:3) yields the desired 3-0-acetyl-6-0-tert.butyldimethylsilyl-glucal in approximately 85% yield (0.98–1.0 g).

10. Preparation of 4-0-acetyl-6-0-tert.butyldimethylsilyl-glucal 1.03 g (3 mmol) of 3,4-di-0-acetyl-6-0-tert.butyldimethylsilyl-glucal in 10 ml of 0.1 M potassium phosphate buffer (pH=7) are stirred with 0.5–1.0 g of lipase P or lipase Fp (Amano), immobilized on $SiO_2$, at room temperature. After the reaction is complete (5–8 h), the immobilized reusable enzyme is separated off. The desired 4-0-acetyl-6-0-tert.butyldimethylsilyl-glucal is obtained either by extraction of the aqueous solution with chloroform or ethyl acetate or after freeze-drying and subsequent chromatography on silica gel (ether/hexane 1:2) in 82% yield.

11. Preparation of 3-0-acetyl-6-0-benzoylglucal 1.0 g (4 mmol) of 6-0-benzoylglucal is taken up in 10–20 mL of vinyl acetate and stirred with 1 g of lipase (Pseudomonas spec.) at room temperature for 5 h. Filtering off the enzyme and crystallization or chromatography on silica gel (ethyl acetate/hexane 1:1) yields 3-0-acetyl-6-0-benzoylglucal in 88–94% yield (1.03–1.10 g).

12. Preparation of 3-0-acetyl-6-benzoylgalactal 1.0 g (4 mmol) of 6-0-benzoylgalactal is taken up in 10–15 ml of dimethoxyethane (DME) and 20–25 ml of vinyl acetate and stirred with 1 g of lipase P at room temperature for 8 h. Filtering off the enzyme and crystallization or chromatography on silica gel (ether/hexane 1:1) yield 3-0-acetyl-6-0-benzoylgalactal in 80–85% yield.

13. Preparation of 6-0-acetyl-3-0-chloroacetyl-glucal 1.03 g (5.5 mmol) of 6-0-acetylglucal are taken up in about 2–5 ml of dimethoxyethane and 10 ml of vinyl chloroacetate and stirred with 1 g of lipase P (Amano) at room temperature for about 2–3 h. Filtering off the enzyme, concentration of the solution and chromatography on silica gel (ether/hexane 1:2) result in 6-0-acetyl-3-0-chloroacetyl-glucal in 80–85% yield.

14. Preparation of 6-0-acetyl-3-0-chloroacetyl-galactal 1.03 g (5.5 mmol) of 6-0-acetylgalactal are taken up in 10–15 ml of DME and 20–25 ml of vinyl chloroacetate and stirred with 1 g of lipase P (Pseudomonas spec.) at room temperature for 5–6 h. Filtering off the reusable enzyme, concentration of the solution and chromatography (SiO2, ether/hexane 1:2) result in 6-0-acetyl-3-0-chloroacetylgalactal in 80% yield.

15. Preparation of 6-0-benzoyl-3-0-chloroacetyl-glucal 1.0 g (4 mmol) of 6-0-benzoylglucal is dissolved in Z-5 ml of dimethoxyethane and 10–15 ml of vinyl chloroacetate and stirred with 1 g of lipase P (Amano) for 1–2 h, Filtering off the enzyme and chromatography on silica gel (ether/hexane 1: 1 ) yield 6-0-benzoyl-3-0-chloroacetylglucal in 82–87% yield.

16. Preparation of 6-0-benzoyl-3-0-chloroacetyl-galactal 1.0 g (4 mmol) of 6-0-benzoylgalactal is taken up in about 20–25 ml of DME and 10–15 ml of vinyl chloroacetate and stirred with 1 g of lipase from Pseudomonas spec. (lipase P, Amano) at room temperature for about 5–7 h. Filtering off the reusable enzyme, concentration of the solution in vacuo and chromatography on silica gel (ether/hexane 1:1) or crystallization result in 6-0-benzoyl-3-0-chloroacetyl-galactal in 80% yield (1050 mg).

17. Preparation of 6-0-benzoylglucal 1.0 g (6.85 mmol) of glucal is taken up in 1.5–2.0 ml of tetrahydrofuran and 3–5 ml of vinyl benzoate and stirred with 1 g of lipase from Candida cylindracea (Amano AY-20) at room temperature for 6 h. Filtering off the enzyme, concentration of the solution in vacuo, taking up the residue in ethyl acetate and extracting it with aqueous NaHCO3 solution, and subsequent chromatography on silica gel (ethyl acetate/hexane 1:1) result in 1.20 g (70%) of the desired 6-0-benzoylglucal.

18. Preparation of 6-0-benzoylgalactal 1.0 g (6.85 mmol) of galactal is taken up in 0.5–1.5 ml of H2O, 8 g of crushed molecular sieves are added, and the mixture is stirred with 1 g of Candida lipase AY-20 (Meito, Sangyo) or 1 g of lipase P (Amano) in 10–15 ml of vinyl benzoate at room temperature for 8–10 h. Filtering off the enzyme, concentration of the solution in vacuo, taking up the residue in ethyl acetate and extracting it with aqueous NaHCO3 solution, and subsequent chromatography on silica gel (ethyl acetate/hexane 1:1) result in 65–68% (about 1130 mg) of the desired 6-0-benzoylgalactal.

19. Preparation of 6-0-acetyl-3-0-methoxyacetylglucal 325 mg (1.73 mmol) of 6-0-acetylglucal are dissolved in 1 ml of dimethoxyethane, 1 ml of vinyl methoxyacetate and 325 mg of lipase Fp (Pseudomonas. fluorescens, Amano) are added, and the mixture is stirred at room temperature for 5½ hours. Filtering off the enzyme and flash chromatography on silica gel (ethyl acetate/hexane 1:2) result in 422 mg (1.62 mmol, 93.8% yield) of the desired 3-0-methoxyacetyl-6-0-acetylglucal.

20. Preparation of 6-0-benzoyl-3-0-methoxyacetylglucal 200 mg (0.8 mmol) of 6-0-benzoylglucal in 1 ml of dimethoxyethane are stirred with 1 ml of vinyl methoxyacetate and 200 mg of lipase Fp from Pseud. fluorescens at room temperature for 3 h.

Filtering off the enzyme and flash chromatography on silica gel (hexane and ether/hexane 1:1) yield 232 mg (0.72 mmol, 90% yield) of the desired 6-0-benzoyl-3-0-methoxyacetylglucal.

21. Preparation of 6-0-acetyl-]-0-phenoxyacetylglucal 318 mg (1.69 mmol) of 6-0-acetylglucal in 1 ml of dimethoxyethane are stirred with 1 ml of vinyl phenoxyacetate and 320 mg of lipase Fp at room temperature for 7 hours.

Filtering off the enzyme and flash chromatography on silica gel (ethyl acetate/hexane 1:2) yielded 478 mg (1.48 mmol), 87.8% yield) of 6-0-acetyl-3-0-phenoxyacetylglucal.

22. Preparation of 6-0-benzoyl-3-0-phenoxyacetylglucal 226 mg (0.90 mmol) of 6-0-benzoylglucal are dissolved in 1 ml of dimethoxyethane and stirred with 1 ml of vinyl phenoxyacetate and 220 mg of lipase Fp at room temperature for 3 hours. Filtration and flash chromatography (silica gel; hexane and ether/hexane 1:1) result in 6-0-benzoyl-3-0-phenoxyacetylglucal in 88% yield (304.5 mg, 0.79 mmol).

23. Preparation of 6-0-benzoyl-3-0-phenacetylglucal 200 mg (0,80 mmol) of 6-0-benzoylglucal are dissolved in 1 ml of dimethoxyethane and stirred with 1 ml of vinyl phenylacetate and 200 mg of Lipase Fp from Pseudomonas fluorescens at room temperature overnight (<20 h). Filtering off the enzyme and purification by chromatography on SiO2 (hexane and ether/hexane 1:1) result in 6-0-benzoyl-3-0-phenacetylglucal in 75–85% yield (220–250 mg).

24. Preparation of 6-0-acetyl-3-0-phenacetylglucal 214 mg (1.14 mmol) of 6-0-acetylglucal are dissolved in 1 ml of dimethoxyethane, and 1 ml of vinyl phenylacetate and 200 mg of lipase Fp are added, and the mixture is stirred at about 20° C. for 48 h. Filtration and chromatography result in 6-0-acetyl-3-0-phenacetylglucal in 80–85% yield (280–297 mg, 0.91–0.97 mmol).

We claim:

1. A process for enzymatic esterification or ester cleavage with the aid of lipases or esterases, which comprises the reaction thereof with unsaturated sugar compounds of the formula I

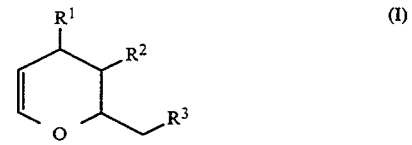

in which
a) $R^1$, $R^2$ and $R^3$ are independently selected from ($C_1$ to $C_{10}$)-acyloxy and benzoyloxy,
b) $R^1$, $R^2$ and $R^3$ are hydroxyl,
c) $R^1$ is a hydroxyl protected by an ester or an ether linkage or is an acetal and $R^2$ and $R^3$ are independently selected from ($C_1$–$C_{10}$)-acyloxy and benzoyloxy,
d) $R^1$ and $R^3$ are independently selected from ($C_1$–$C_{10}$)-acyloxy and benzoyloxy and $R^2$ is a hydroxyl protected by an ester or an ether linkage or is an acetal,
e) R is a hydroxyl protected by an ester or an ether linkage or is an acetal and $R^2$ and $R^3$ are hydroxyl,
f) $R^1$ and $R^3$ are hydroxyl and $R^2$ is a hydroxyl protected by an ester or an ether linkage or is an acetal,
g) $R^1$ and $R^2$ are hydroxyl and $R^3$ is ($C_1$–$C_{10}$)-acyloxy, benzoyloxy or a hydroxyl protected by an ester or an ether linkage or is an acetal, or
h) $R^1$ and $R^2$ are independently selected from acyloxy and benzoyloxy and $R^3$ is a hydroxyl protected by an ester or an ether linkage or is an acetal.

2. The process as claimed in claim 1, wherein the acyloxy group has a chain length of $C_1$ to $C_5$.

3. The process as claimed in claim 1, wherein lipases and esterases from microorganisms or from the pancreas or liver of animals are used.

4. The process as claimed in claim 3, wherein lipases or esterases from Pseudomonas, Candida, Mucor, Rhizopus, Penicillium and Aspergillus are used, as well as from pig liver and pig pancreas.

5. The process as claimed in claim 3, wherein lipases or esterases from Candida are used for reaction with primary functional groups of the compounds of the formula I, and lipases or esterases from Pseudomonas are used for reaction with secondary functional groups of the said compounds.

6. The process as claimed in claim 5, wherein in the compound of the formula I $R^1$ and $R^2$ are secondary functional groups and $R^3$ is a primary functional group.

7. The process as claimed in claim 1, wherein the carbon atoms of the acyloxy group are independently substituted with a member selected from the group consisting of halogen, amino, methoxy, phenyl and phenoxy.

8. The process as claimed in claim 1, wherein the carbon atoms of the benzoyloxy group are independently substituted with a member selected from the group consisting of nitro, halogen and ($C_1$ and $C_2$)-alkoxy.

9. A process for enzymatic esterification which comprises adding a benzoyl or acyl donor to an unsaturated sugar compound of the formula I

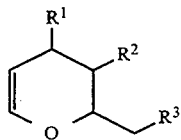
(I)

in which $R^1$, $R^2$ and $R^3$ are hydroxyl $R^1$ is a hydroxyl protected by an ester or an ether linkage or is an acetal and $R^2$ and $R^3$ are hydroxyl, $R^1$ and $R^3$ are hydroxyl and $R^2$ is a hydroxyl protected by an ester or an ether linkage or is an acetal, or $R^1$ and $R^2$ are hydroxyl and $R^3$ is ($C_1$-$C_{10}$)-acyloxy, benzoyloxy or a hydroxyl protected by an ester or an ether linkage or is an acetal, and adding thereto and incubating therewith a lipase or esterase in free or immobilized form.

10. The process as claimed in claim 9 in which the benzoyl or acyl donor is a carboxylic ester or carboxylic anhydride.

11. The process as claimed in claim 9 in which the incubation is carried out at a temperature between 0° and 80° C.

12. The process as claimed in claim 11 in which the incubation is carried out at a temperature between 10° and 50° C.

13. The process as claimed in claim 9 in which the reaction time is between 0.5 hour and 3 days.

14. The process as claimed in claim 13 in which the reaction time is between 5 and 24 hours.

15. A process for enzymatic ester cleavage, which comprises adding a lipase or esterase to an unsaturated sugar compound of the formula I

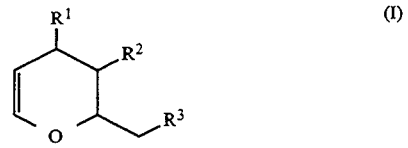
(I)

in which $R^1$, $R^2$ and $R^3$ are independently selected from ($C_1$ to $C_{10}$)-acyloxy and benzoyloxy, $R^1$ is a hydroxyl protected by an ester or an ether linkage or is an acetal and $R^2$ and $R^3$ are independently selected from ($C_1$-$C_{10}$)-acyloxy and benzoyloxy, $R^1$ and $R^3$ are independently selected from ($C_1$-$C_{10}$)-acyloxy and benzoyloxy and $R^2$ is a hydroxyl protected by an ester or an ether linkage or is an acetal, $R^1$ and $R^3$ are hydroxyl and $R^2$ is a hydroxyl protected by an ester or an ether linkage or is an acetal, or $R^1$ and $R^2$ are independently selected from acyloxy and benzoyloxy and $R^3$ is a hydroxyl protected by an ester or an ether linkage or is an acetal, and incubating the lipase or esterase therewith.

16. The process as claimed in claim 15 in which the reaction is operated at a constant pH or without pH control in the range of about 4 to 8.

17. The process as claimed in claim 15 in which the ester cleavage is carried out with an unsaturated sugar compound of the formula Ia) and a lipase or esterase of Pseudomonas.

* * * * *

UNITED STATES PATENT AND TRADEMARK OFFICE
CERTIFICATE OF CORRECTION

PATENT NO. : 5,380,659
DATED : January 10, 1995
INVENTOR(S) : Wolfgang HOLLA et al.

It is certified that error appears in the above-indentified patent and that said Letters Patent is hereby corrected as shown below:

Claim 1, Column 8, Line 59 "R" should read --$R^1$--.

Claim 3, Column 9, Line 4 "and" should read --or--.

Signed and Sealed this

Second Day of July, 1996

Attest:

BRUCE LEHMAN

*Attesting Officer*　　　*Commissioner of Patents and Trademarks*